United States Patent [19]

Stevens et al.

[11] Patent Number: 4,892,598
[45] Date of Patent: Jan. 9, 1990

[54] METHOD OF INTEGRATING AN ABSORBENT INSERT INTO AN ELASTOMERIC OUTER COVER OF A DIAPER GARMENT

[75] Inventors: Robert A. Stevens, Appleton; Leona G. Boland, Neenah; John L. Chiatalas, Appleton, all of Wis.

[73] Assignee: Kimberly-Clark Corporation, Neenah, Wis.

[21] Appl. No.: 140,264

[22] Filed: Dec. 30, 1987

[51] Int. Cl.$^4$ .............................................. B32B 31/04
[52] U.S. Cl. ...................................... 156/91; 156/160; 156/163; 604/385.1; 604/385.2; 604/397; 604/399
[58] Field of Search ............... 156/91, 252, 253, 308.2, 156/160, 163, 229; 604/365, 366, 385.1, 385.2, 386, 387, 391, 393, 397, 399

[56] References Cited

U.S. PATENT DOCUMENTS

| | | | |
|---|---|---|---|
| 2,141,105 | 12/1938 | Eller et al. | 128/284 |
| 2,544,726 | 3/1951 | Rogatz | 128/287 |
| 2,936,758 | 5/1960 | Csulits | 128/284 |
| 3,196,874 | 7/1965 | Hrubecky | 128/287 |
| 3,370,590 | 2/1968 | Hokanson et al. | 128/290 |
| 3,509,881 | 5/1970 | Sabee | 128/287 |
| 3,566,870 | 3/1971 | Benjamin | 604/399 |
| 3,599,640 | 8/1971 | Larson | 128/286 |
| 3,644,157 | 2/1972 | Draper | 156/160 |
| 3,653,381 | 4/1972 | Warnken | 128/284 |
| 3,658,064 | 4/1972 | Pociluyko | 128/287 |
| 3,805,790 | 4/1974 | Kaczmarzyk et al. | 128/290 |
| 3,860,003 | 1/1975 | Buell | 128/287 |
| 3,882,871 | 5/1975 | Taniguchi | 128/287 |
| 4,022,210 | 5/1977 | Glassman | 128/284 |
| 4,036,233 | 7/1977 | Kozak | 128/287 |
| 4,050,462 | 9/1977 | Woon et al. | 128/287 |
| 4,166,464 | 9/1979 | Korpman | 128/287 |
| 4,205,679 | 6/1980 | Repke et al. | 128/287 |
| 4,324,245 | 4/1982 | Mesek et al. | 128/287 |
| 4,338,939 | 7/1982 | Daville | 128/286 |
| 4,355,425 | 10/1982 | Jones et al. | 2/402 |
| 4,397,646 | 8/1983 | Daniels et al. | 604/381 |
| 4,425,128 | 1/1984 | Motomura | 604/381 |
| 4,496,360 | 1/1985 | Joffe et al. | 604/397 |
| 4,525,407 | 6/1985 | Ness | 428/138 |
| 4,555,244 | 11/1985 | Buell | 604/385.2 |
| 4,573,991 | 3/1986 | Pieniak et al. | 604/385 A |
| 4,597,760 | 7/1986 | Buell | 604/397 |
| 4,597,761 | 7/1986 | Buell | 604/397 |
| 4,606,964 | 8/1986 | Wideman | 428/152 |
| 4,615,695 | 10/1986 | Cooper | 604/385 |
| 4,636,207 | 1/1987 | Buell | 604/370 |
| 4,642,110 | 2/1987 | Dudek | 604/385.1 |
| 4,657,539 | 4/1987 | Hasse | 604/385 A |
| 4,662,877 | 5/1987 | Williams | 604/385 A |
| 4,701,176 | 10/1987 | Wilson et al. | 604/385.2 |
| 4,747,846 | 5/1988 | Boland et al. | 604/385.1 |
| 4,756,709 | 7/1988 | Stevens | 604/385.1 |
| 4,770,656 | 9/1988 | Proxmire et al. | 604/393 |

FOREIGN PATENT DOCUMENTS

| | | | |
|---|---|---|---|
| 558763 | 4/1960 | Belgium | 604/397 |
| 0155515 | 2/1985 | European Pat. Off. | |

Primary Examiner—Caleb Weston
Attorney, Agent, or Firm—John L. Chiatalas

[57] ABSTRACT

A method of integrating a fluid-absorbing component into a holding component of an anatomically form-fitting, generally self-adjusting absorbent garment is disclosed. An elastomeric outer cover is provided for holding a relatively inelastic absorbent insert in selected bodily registration for absorbing and containing bodily fluids. A slidable hem retaining arrangement operatively connects the insert to the outer cover, including cooperating fasteners engageable with one another through a plurality of fenestrations, allowing unrestricted elongation or retraction of the outer cover relative to the insert. The fasteners are releasably engageable with one another to allow removal and replacement of the insert when soiled. Alternatively, ultrasonic bonds may be used instead of refastenable closures, where a single-use disposable garment is contemplated.

28 Claims, 10 Drawing Sheets

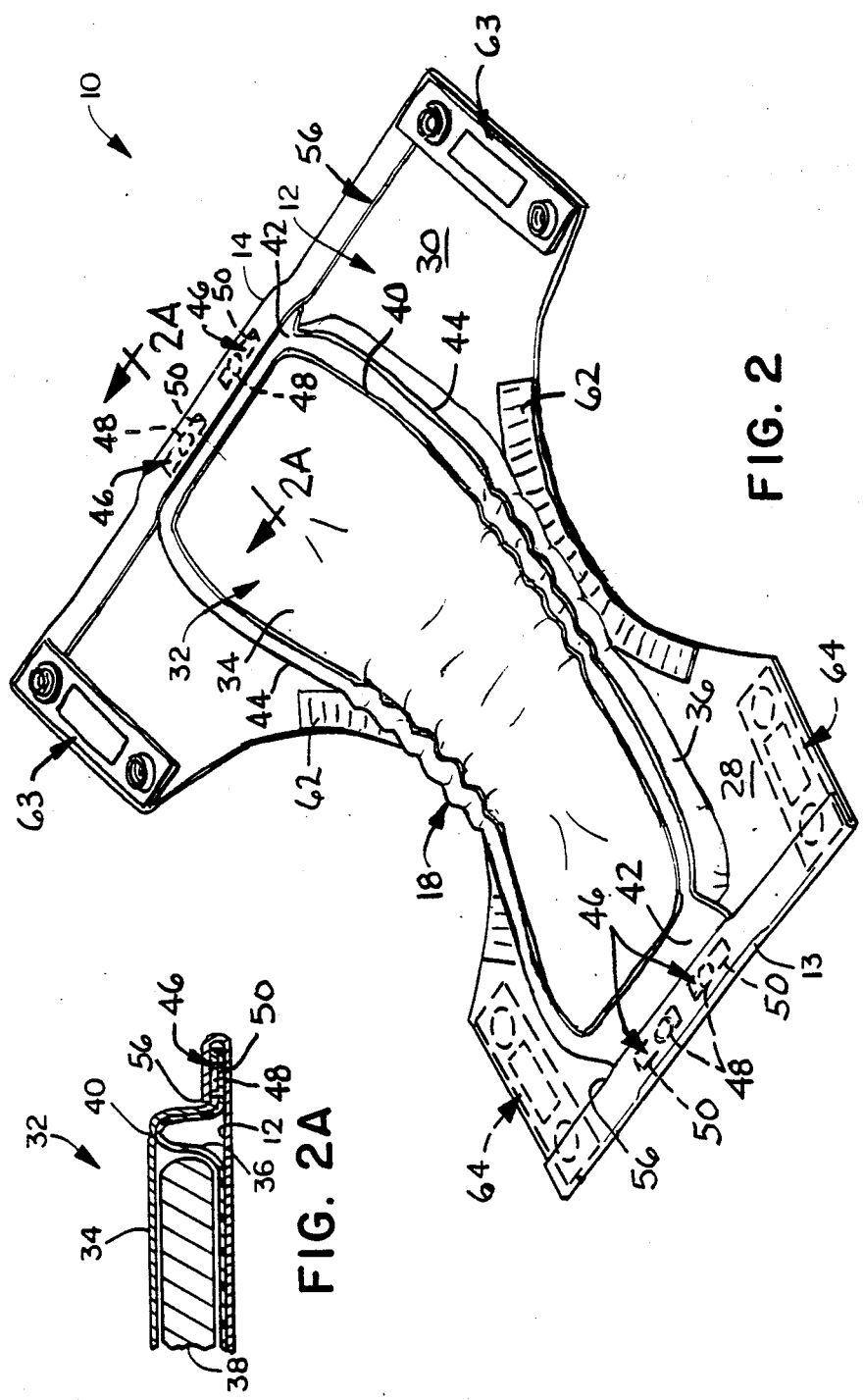

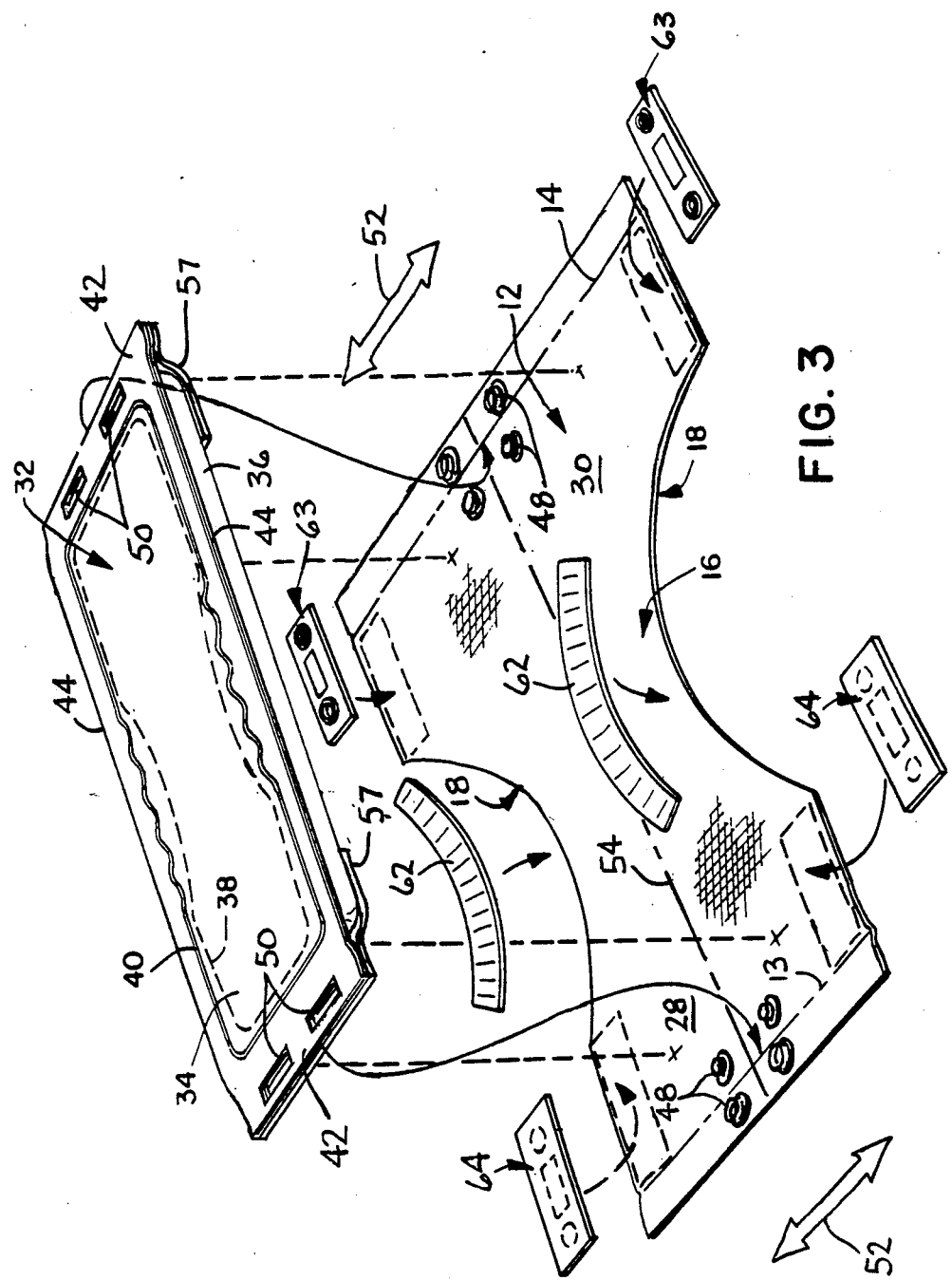

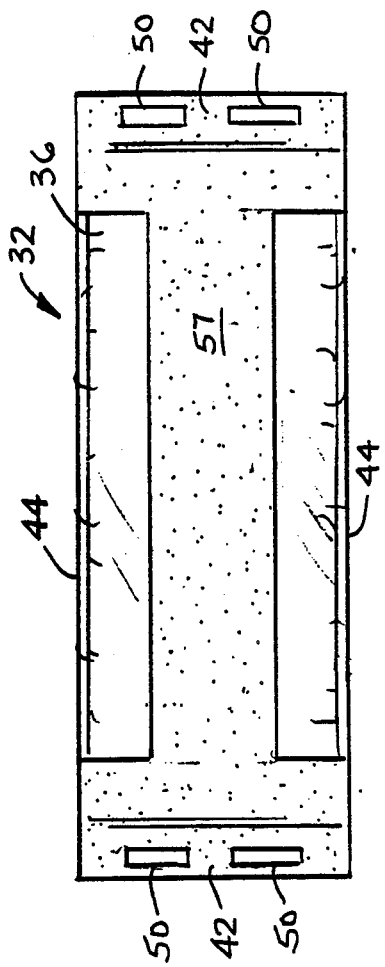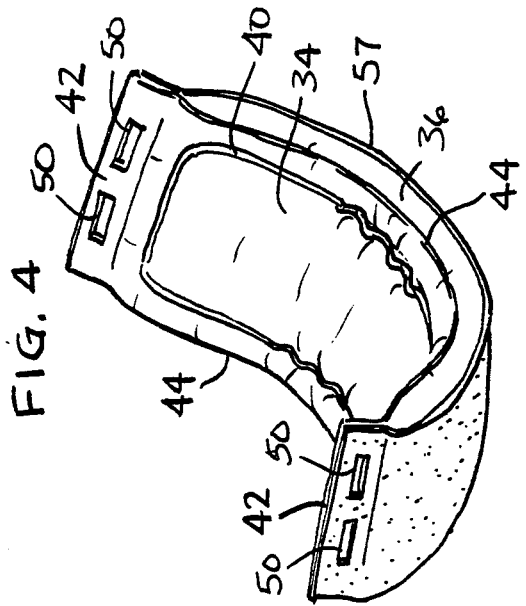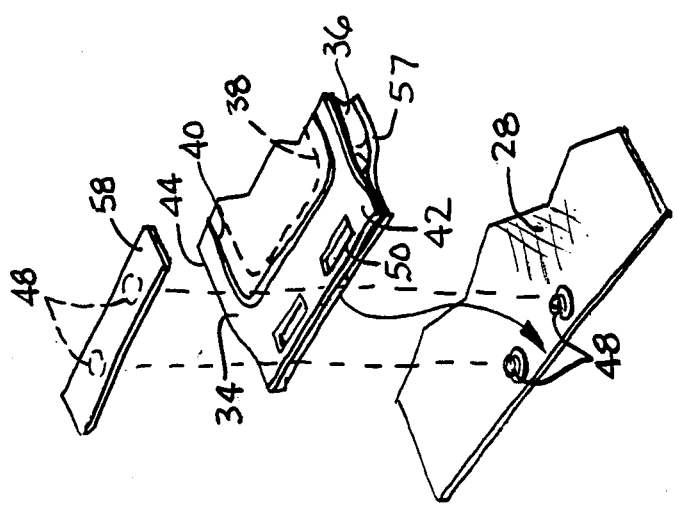

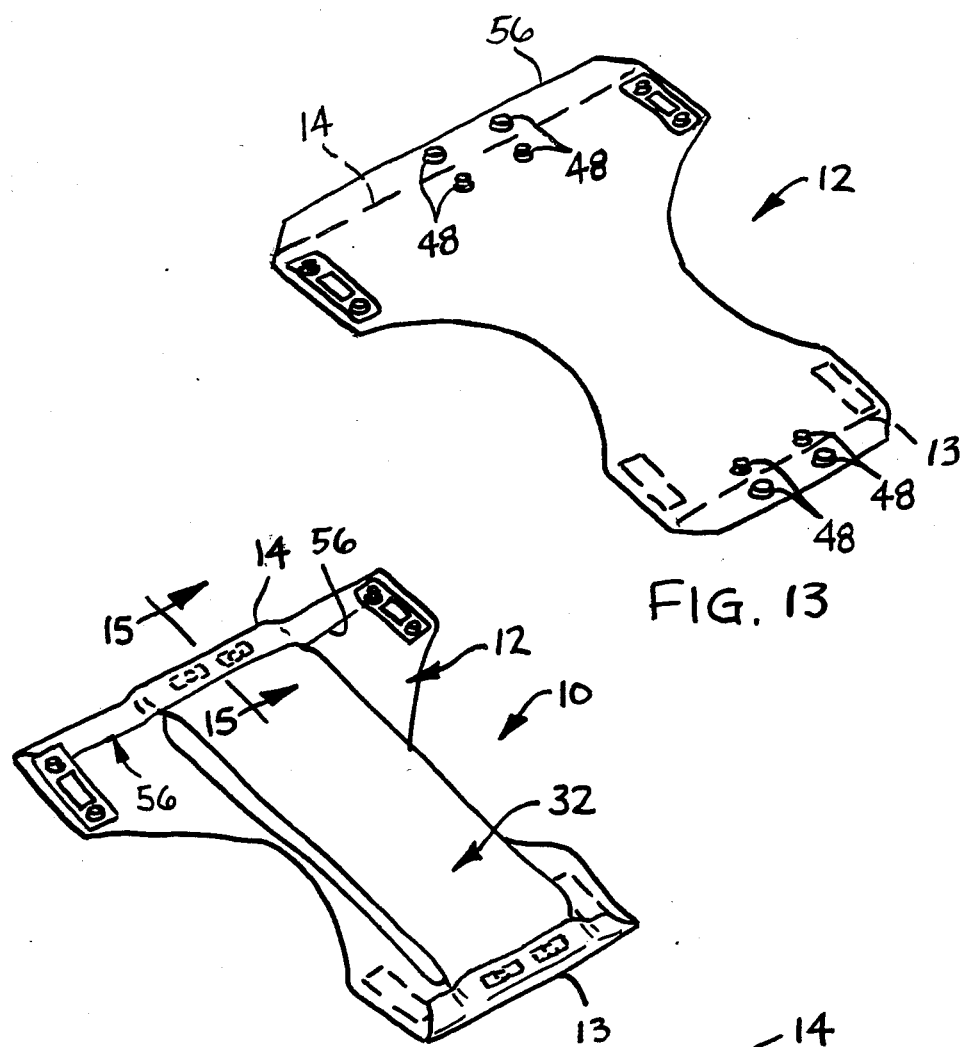
FIG. 13
FIG. 14
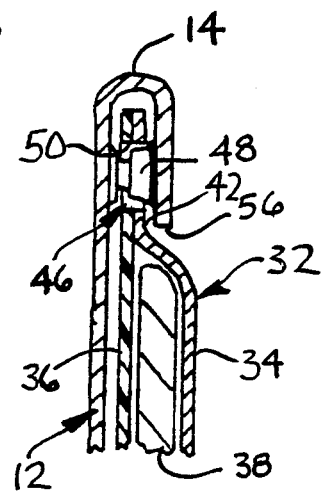
FIG. 15

METHOD OF INTEGRATING AN ABSORBENT INSERT INTO AN ELASTOMERIC OUTER COVER OF A DIAPER GARMENT

TECHNICAL FIELD

The present invention relates, generally, to the field of disposable garments utilized for the absorption and containment of urine and other bodily exudates. More particularly, the present invention relates to absorbent garments having elastic outer holders positioning a disposable pad on the body.

BACKGROUND OF THE INVENTION

This invention is an improvement upon the disposable garment of U.S. patent application Ser. No. 947,941 in the name of Deborah L. Proxmire, et al., and Stevens U.S. Pat. No. 4,701,172, both assigned to the assignee of the instant application, the entire disclosures of which are expressly incorporated herein by reference and relied upon.

Disposable garments are generally well known in the art and have become an important and an essentially indispensable sanitary protection item, most particularly in the field of infant and child care where disposable diapers provide for the absorption and containment of urine and other bodily exudates. Present commercially available disposable diapers are generally unitary, preshaped and prefolded, and comprised of a porous facing layer, a fluid impervious backing sheet with an absorbent material disposed therebetween. These presently available disposable diapers have met a particular need and have become ever increasingly popular. However, even though the present available disposable diapers have achieved a certain degree of efficiency and effectiveness, several draw-backs remain that have been identified by mothers of infants wearing the diapers. These mothers have strongly voiced their desire to be able to obtain disposable diapers that are aesthetically neat and attractive when on their infant or child. The aesthetically neat criteria have been identified as including a trim, slim fit, and a neat fitting waist and legs that do not allow leakage of urine or feces. It has also been found that mothers do not want their children looking rumpled, bulky or messy. In addition, these mothers have expressed the desire to either have a disposable diaper that fits more sizes of babies or to have disposable diapers provided in more sizes. Another draw-back identified by these mothers has been the problem associated with skin irritation caused by urine, feces or moisture trapped next to the skin. They have again been very vocal in their desire to obtain disposable diapers that avoid or solve this problem.

A variety of prior diaper constructions have used leg or waist gathers. For example, Mesek, et al. U.S. Pat. No. 4,324,245, discloses a gathered or bloused design wherein waterproof extruded elastic film is applied to the waist and leg areas of a film barrier backsheet having an absorbent adhered thereto so that the elastic deforms the absorbent structure; again, such an arrangement represents the current state of disposable diapers on the market. Others include Hrubecky U.S. Pat. No. 3,196,872 showing a rectangular diaper provided with triangular-shaped infolds in the crotch area, Buell U.S. Pat. No. 3,860,003 wherein the diaper edges are provided with elasticized, flexible flaps along the edge of the absorbent pad in the crotch region and Woon, et al. U.S. Pat. No. 4,050,462 wherein the diaper is elasticized only along the edges in the narrowed crotch area to create gross transverse rugosities in the crotch area.

Prior art constructions, such as Pociluyko U.S. Pat. No. 3,658,064, Hokanson, et al. U.S. Pat. No. 3,370,590 and Davilla U.S. Pat. No. 4,338,939, have attempted to provide waste containment with a reusable liquid impermeable diaper cover having waterproof pouches, retaining flaps or pockets for freely receiving an absorbent, such as a traditional cloth diaper or disposable absorbent; however, the retaining pouches on these supporting garments occlude the skin, covering the target areas at which urine is excreted. Motomura U.S. Pat. No. 4,425,128, discloses a diaper cover with sections of waterproof, stretchable material in the ears of the cover adjacent the fasteners. Eller U.S. Pat. No. 2,141,105 also discloses an elastic woven diaper cover having elastic retaining straps for holding a pad at the ends thereof. In summary these prior art diaper holders rely upon reuseable treated woven fabrics, many having seams fully integrating other nonstretchable absorbent components between stretchable cover portions, thereby effectively eliminating any stretch properties in the front or rear panels or along the waist and leg openings of the diaper cover. Moreover, there is no recognition of a functional absorbent structure integrated into a stretchable outer cover providing cooperative interactions therebetween to enhance the fit, appearance and containment of the diapering system.

Other approaches have utilized elastic fluid impermeable backing films laminated to an absorbent layer in an attempt to provide enhanced conformability to the body surface, but these films are occlusive to the skin, there is no cooperation of elements elucidated and the integration of the absorbent component restricts the elasticity of the outer cover by the manner in which it is bonded thereto. In this type of construction, the elastic backing film must provide both the barrier function and the fit and conformability functions of the diaper. Such an absorbent dressing is taught by Korpman U.S. Pat. No. 4,166,464.

Daniels, et al. U.S. Pat. No. 4,397,646 discloses a reuseable unitary diaper capable of repeated sterilizations in a diaper laundry, comprising elasticized end and side margins and a durable absorbent such as cotton sewn into the crotch area of the waterproof diaper cover, which is a Teflon ® coated polyester or equivalent woven material.

It has been known to attach absorbent pads to diaper holders and/or fasten diapers about wearers by using various fastening arrangements. For example, Rogaty U.S. Pat. No. 2,544,726 uses snaps; Clifford U.S. Pat. No. 2,366,440 uses braces to suspend the diaper pants; and Mann U.S. Pat. No. 3,077,193 uses press studs to mount a diaper in position within a knit holder.

U.S. Pat. Nos. 4,597,761, 4,496,360 and 4,597,670 all disclose multi-component diapering systems comprising a disposable absorbent capable of attachment to a reusable overgarment. Jones, et al. U.S. Pat. No. 4,355,425, which uses a melt-blown elastic border strip, and Draper U.S. Pat. No. 3,644,157 both disclose disposable stretchable panties or shorts unsuitable for use as diapering garments.

Pieniak U.S. Pat. No. 4,573,991 discloses a reticulated elastic member secured between the facing and film backing sheets of a diaper. Wideman U.S. Pat. No. 4,606,964 discloses a pleated web bonded to an elastomeric film, however, breathability is not simultaneously imparted to the composite by the bonding process. Various non-elastomeric films require stretching to impart porosity therein. Ness U.S. Pat. No. 4,525,407 discloses a laminate rendered elastic by stretching.

U.S. Pat. No. 3,805,790 discloses a pre-shaped, three-dimensionally formed absorbent article which assumes the contours of a wearer.

Hence, present commercially available disposable diapers utilizing stretchable backsheets functioning both as the pad holder and liquid barrier have inadequately recognized the associated problems of a unitary construction. Prior art reuseable diaper holders for holding a pad do not address the many substantial interactive concerns presented by a separate absorbent insert, stretchable outer cover and a fastening system.

SUMMARY OF THE INVENTION AND ADVANTAGES

According to the instant invention, there is provided a method of integrating a fluid-absorbing component into a holding component of an anatomically form-fitting and generally self-adjusting diaper garment. The method comprises the steps of providing a resiliently stretchable positioning means for holding and positioning the absorbing component during use, delimiting a shape having front and rear sections, an intermediate crotch section, a pair of leg openings along opposed marginal edges of the crotch section and front and rear panels separated from one another by the crotch section. Absorbent insert means are provided for absorbing and containing bodily fluids and other wastes, delimiting a shape superposable on the outer cover means and having opposed longitudinal ends and a pair of sides extending between and interconnecting the ends. Cooperable retaining means are provided on the insert means and the outer cover means, respectively, for retention of the insert means by the positioning means. The method of the invention further comprises the steps of providing fastening means and slot-forming means adapted for receiving the fastening means therethrough while allowing substantially unrestricted functional elongation and retraction of the positioning means relative to the insert means. The insert means is superposed on an inner body-facing surface of the outer cover means, and the fastening means are fastened together through the slot-forming means, thereby integrating the insert means with the positioning means to form the present diaper garment.

In a preferred embodiment, the method of the present invention further comprises the step of providing the fastening means with fastenable and refastenable closure means and providing a disposable insert means adapted for removal and replacement thereof.

In another preferred embodiment, the method further comprises the steps of providing an elastomeric outer cover which is resiliently stretchable in a given direction and further wherein the slot-forming means define a major axis which is parallel to the selected direction of stretch provided in the outer cover.

In a further embodiment of the invention, the method further comprises the steps of providing a slidable hem adapted for containing the fastening means and entrapping the slot-forming means therein, engaging the fastening means through the slot-forming means to provide unrestricted functional stretchability of the outer cover means in a selected direction relative to the insert means.

An advantage of the instant invention is that an elastomeric diaper holder and a relatively inelastic absorbent insert may be integrated together without restricting the functional stretch of the diaper holder.

Another advantage of the instant method is that the disposable insert may be suitably adapted so as to be readily unfastened and replaced within a reuseable elastomeric holder by a fresh insert.

BRIEF DESCRIPTION OF THE DRAWINGS

While the specification concludes with claims particularly pointing out and distinctly claiming the subject matter regarded as forming the present invention, it is believed the invention will be better understood from the following descriptions taken in conjunction with the accompanying drawings in which:

FIG. 2 is an internal perspective view of the invention;

FIG. 2A is a sectional view of cross-section 2A—2A of FIG. 2;

FIG. 3 is a partial exploded perspective view of FIG. 2;

FIG. 3A is an exploded perspective view of an end of the garment showing a separate integration member of the present invention;

FIG. 4 is a back view of the absorbent insert of the present invention;

FIG. 4A is a perspective view of the absorbent insert of the present invention, showing a three-dimensionally formed backing;

FIG. 13 is an internal perspective view of the invention showing an outer cover provided in conjunction with a method of using the present invention;

FIG. 14 is a sequential view of the garment of the present invention showing an insert being integrated thereinto according to the method of using the present invention;

FIG. 15 is a sectional view of the garment of the present invention taken along the lines 14A—14A of FIG. 14.

DETAILED DESCRIPTION OF THE PREFERRED EMBODIMENTS

Figure 1:
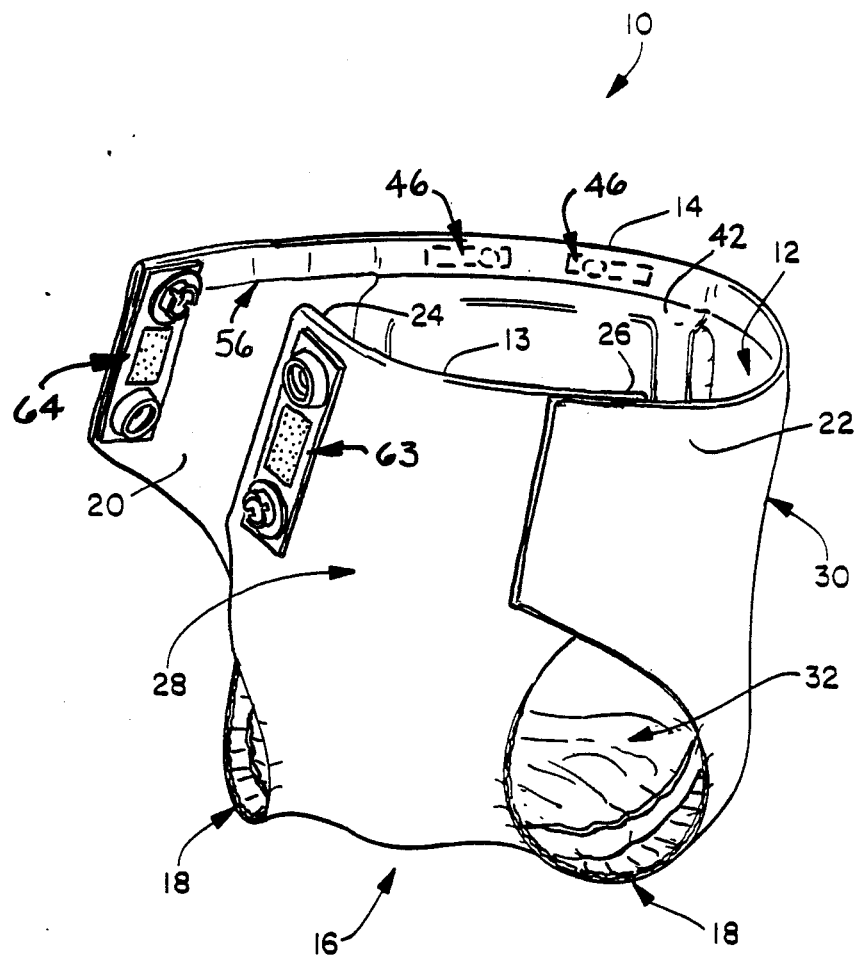
FIG. 1 is a perspective view of the invention.
Figure 5:
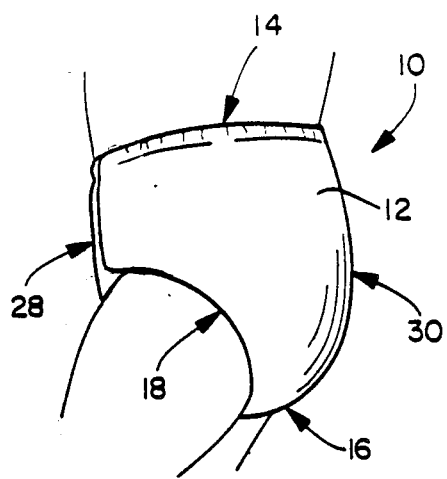
FIG. 5 is a side view of the disposable absorbent garment of the present invention shown secured around a baby.
Figure 6:
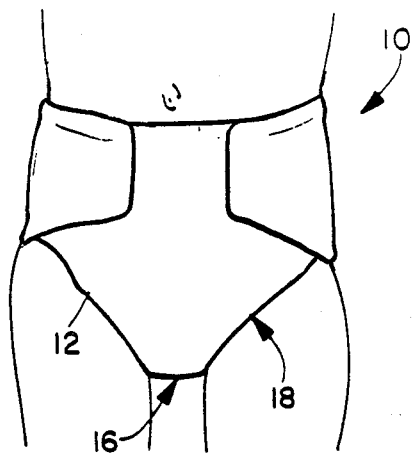
FIG. 6 is a front view of the disposable absorbent garment of the present invention shown secured around a baby.
Figure 7:
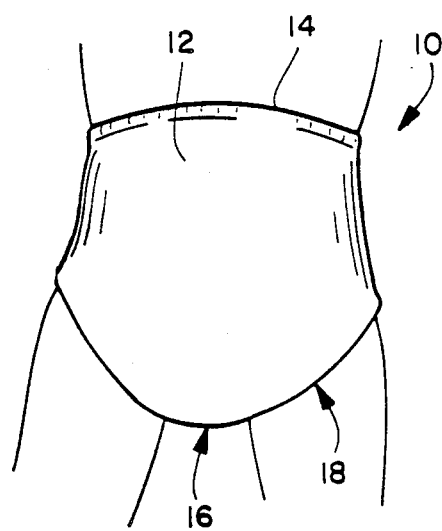
FIG. 7 is a back view of the disposable absorbent garment of the present invention shown secured around a baby.
Figure 8:
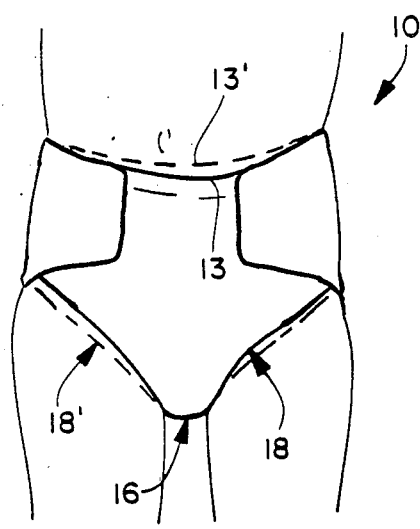
FIG. 8 is a front view of the disposable absorbent garment of the present invention showing the disposition of the garment on the baby after being worn for a period of time.
Figure 9:
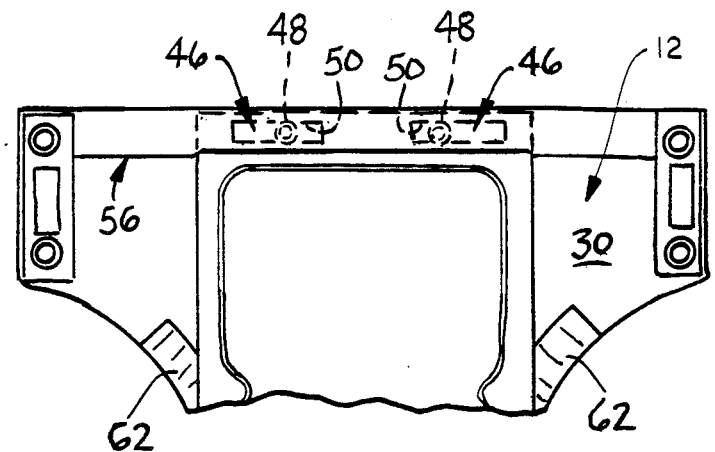
FIG. 9 is a partial internal plan view of one end of the garment of the present invention shown in the unstretched condition.
Figure 10:
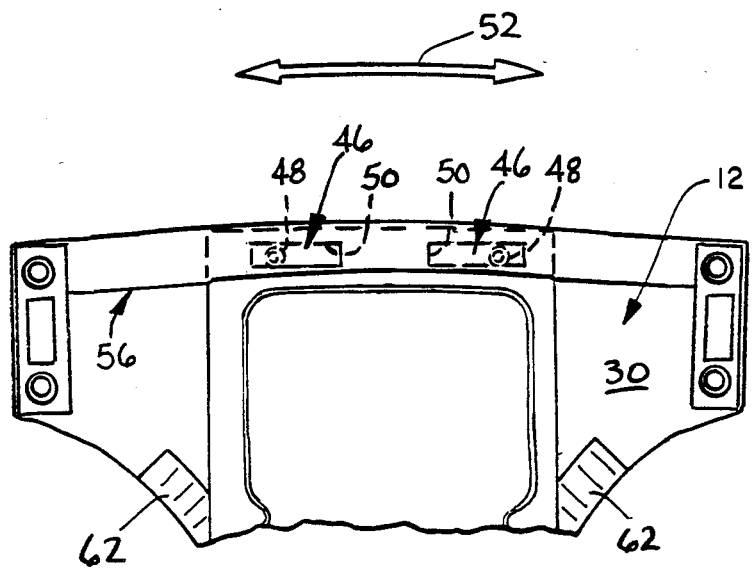
FIG. 10 is a sequential view of FIG. 9 showing the garment of the present invention in a stretched condition.

According to the instant invention, there is provided in FIG. 1 a disposable absorbent garment, generally indicated at 10, such as an infant or adult diaper. The garment is anatomically form-fitting and generally self-adjusting to the body of a wearer as will be understood from a reading of the following description. An elastomeric positioning means, such as the outer cover 12, is provided for holding an absorbent insert means, generally indicated at 32, in a selected registration with the body of a wearer for absorbing and containing bodily fluids. The positioning means includes front 13 and rear 14 waist areas defining an elastically contractible or expansible waist opening, an intermediate crotch area generally indicated at 16, a pair of leg openings, each generally indicated at 18, elastically contractible or expansible along opposed marginal edges of said crotch area 16 which is narrowed, defining a generally hourglass shape with laterally opposed rear ear portions 20, 22 which are engageable with a corresponding pair of front ear portions 24, 26 about a wearer. Front 28 and rear 30 panels are further delimited by the positioning means and are opposed from one another when the garment is secured together as shown in FIG. 1. The front 28 and rear 30 panels are separated from one another by the crotch area.

With continuing reference to FIG. 1 and more specific reference to FIGS. 2 and 2A, the absorbent insert means 32 for absorbing and containing bodily fluids comprises a liquid-permeable, body-facing means 34 for allowing passage of liquid or liquified waste while presenting a body-contacting surface substantially free of liquid pooling. The body-facing means may be in the form of a diaper liner made of, for example, spunbonded polypropylene fibers. The facing means 34 is substantially coterminous with a liquid-impermeable backing means 36, which may be any of a number of film materials, for example, polypropylene film. A liquid-absorbing core means 38 is disposed between the facing 34 and backing 36 means of the absorbent insert and a continuous bond 40 secures the facing 34 and liner 36 means together about the perimeter of the core means 38 to seal the absorbent insert against leakage of waste fluids therefrom. The insert means 32 further defines a shape having opposed longitudinal ends 42, a pair of sides 44 extending between and interconnecting the ends 42 and being superposable on a body-facing surface of the positioning means. The core means 38 of the absorbent insert means 32 may be composed of fibrous absorbent material mixed with particulate hydrogel polymeric material, for example, a superabsorbent polyacrylate particulate material may be employed in a matrix of introfying pulp fluff fibers then compressed to form an absorbent batt having sufficient structural integrity during use.

Referring to FIG. 2, there is provided slidable retaining means, generally indicated at 46, for operatively connecting said insert means 32 to said positioning means 12, including cooperating fastening means 48 for attaching and integrating said insert means 32 and positioning means 12 together and slot-forming means for receiving said fastening means therethrough while allowing substantially unrestricted functional elongation or retraction of said positioning means relative to said insert means. The slot-forming means preferably comprise a plurality of elongated fenestrations 50 formed either in the ends 42 of the insert 32, as shown in FIG. 3, or, alternatively, the fenestrations may be formed in the waist areas 13, 14 of the outer cover and the fastening means 48 may be located on the absorbent insert ends 42 (not shown). The positioning means 12 preferably comprises a nonwoven elastomeric laminar fabric which is resiliently stretchable from about 20% to about 200% in a direction indicated by the arrows 52, essentially transverse to a line centered on the longitudinal axis 54 of the garment 10.

Figure 11:
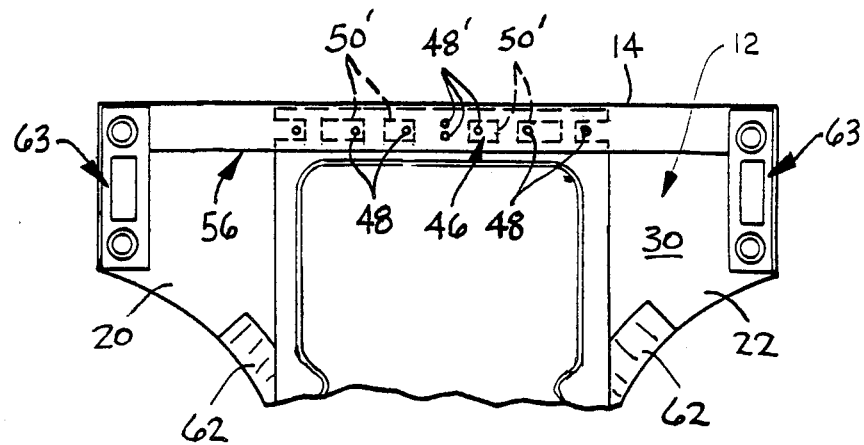
FIG. 11 is a partial internal plan view of an end of the garment of the present invention shown prior to stretching.
Figure 12:
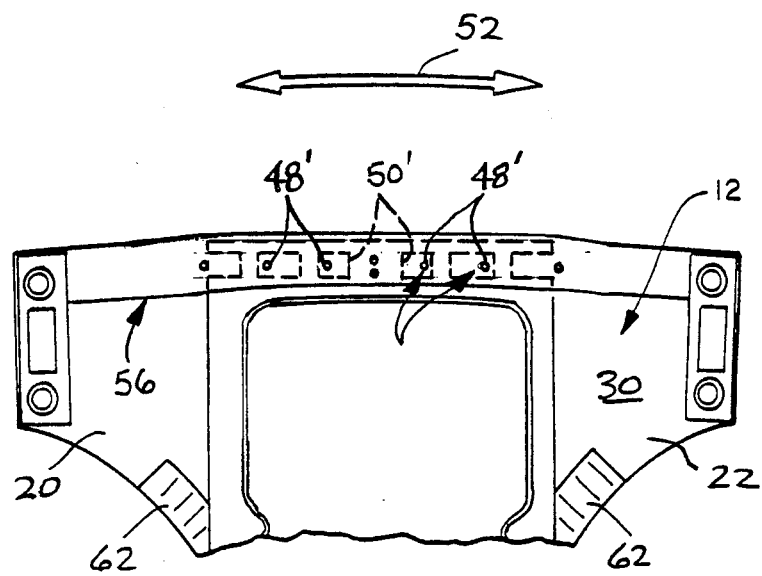
FIG. 12 is a sequential view of FIG. 11 showing the garment of the present invention in a stretched state.

The fastening means preferably comprise refastenable closure means which are releasably engageable with one another through the fenestrations 50 to integrate the insert means 32 and outer cover 12 together. The fastening means may also comprise autogenous bonds 48' as shown in FIGS. 11 and 12.

As shown in FIG. 2, the slot-forming means are located at each of the ends 42 of the insert means 32 and the fastening means are located at associated ones of the waist sections 13, 14, respectively. Referring to FIG. 2A, hem-forming means generally indicated at 56 are provided for entrapping the fenestrations 50 and presenting cooperating fastening means 48 which are engageable through the fenestrations 50. Preferably, as mentioned above, the fastening means comprise closure means fastenable and refastenable with one another for removing and replacing the insert means when the same becomes soiled; however, the garment 10 may be completely disposable, that is, the outer cover nonreusable, in the case where the fastening means comprise autogenous bonds 48' (FIGS. 11 and 12).

Figures 19A, 19B, 19C:
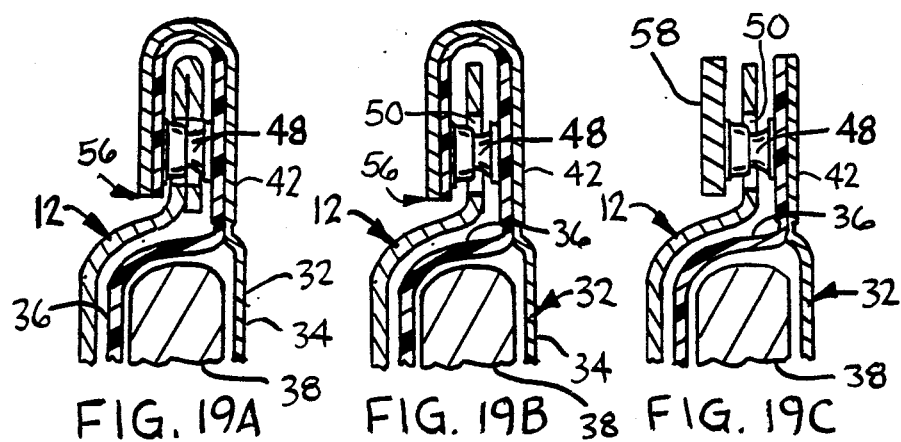
FIG. 19A is a sectional view showing an alternative method of integrating the garment of the present invention wherein the fenestrations are formed in the outer cover.
FIG. 19B is a sectional view showing another alternative method of integrating the garment of the present invention wherein the fenestrations are formed in the outer cover.
FIG. 19C is a sectional view showing another alternative method of integrating the garment of the present invention wherein the fenestrations are formed in the outer cover.

Referring to FIGS. 19A-19C, the fastening means may be located at the ends 42 of the absorbent insert means 32 and the fenestrations 50 may be located at associated ones of said waist sections, respectively, of which a representative waist section 14 is shown. The waist section 14 may also be hemmed (FIG. 19A) for added strength surrounding the fenestrations 50. Hem-forming means 56 may be provided at the ends 42 for entrapping the slot-forming means located along the waist areas and presenting the fastening means for engagement therethrough. It is further preferred that the fastening means 48 which are fastenable and refastenable with one another comprise cooperating pairs of suitable plastic snap-in fastening elements as are shown in the FIGS. 19A-19C.

Although the outer cover 12 i shown in FIG. 3 as being resiliently stretchable in an essentially cross-body direction 52, and the elongated fenestrations 50 elongated in a correspondingly cross-body direction, the outer cover may alternatively be resiliently stretchable in a longitudinal direction (not shown) essentially parallel to the longitudinal axis 54 of garment 10 depending on the fit characteristics desired, in which case, the fenestrations 50 are elongated in a direction essentially parallel to the longitudinal axis of the garment to provide unrestricted stretch thereof. Although a pair of fenestrations 50 are shown in FIGS. 1–4 and 9–10, a plurality of fenestrations or windows 50' may be used (FIGS. 11–12).

Further according to the instant invention, the backing means 36 may include a flexible, three-dimensional shape-retaining means 57 for maintaining the insert means 32 in a three-dimensional, body-conforming orientation during wear, as shown in FIG. 4.

With further reference to FIGS. 4 and 4A, the three-dimensional shape-retaining means 57 may be configured in an I-shape and be an addition to the film barrier 36, also providing a reinforcing function to the ends 42 of the insert in order to prevent tearing or ripping of the fenestrations 50 by their association with the fastening means 48. The shape-retaining means 57 may be formed of a foam material such as Volara TM, manufactured by Voltek, Inc., which is thermoformed by techniques known by the art into a three-dimensional shape. Alternatively, the shape-retaining means 57 may be a complete liquid-impermeable shell of such foam material, eliminating the need for a separate barrier material 36, since the foam may adequately provide both shape-retaining, reinforcing and liquid barrier functional properties to the absorbent insert 32.

Referring to FIG. 4A, wherein the absorbent insert means assumes a three-dimensional shape-retaining conformation due to the backing shell 57, the backing shell 57 may be provided with undercut edges, that is, a Z-shaped cross along the leg openings (not shown) in order to yield a gasketing effect therealong to limit the sideways flow of fecal material. It is important to keep fecal material and other wastes off the outer cover 12 in order to maintain it reuseable. The instant invention accomplishes this by properly positioning the absorbent insert means 32 to completely contain body wastes, thus allowing the outer cover to remain free of contamination. It will be understood that the I-shaped reinforcing means 57 can be formed in a two-dimensional shape and provide a reinforcing function for the fenestrations 50 at the ends 42 of the insert means 32, in which case the foam may form a very thin layer.

With reference to FIG. 3A, an alternative means of integrating the garment 10 is shown, whereby a separate integration member 58 is provided bearing snap-in type elements engageable with corresponding elements of the fastening means 48 which are engageable through the fenestrations 50 aligned therewith. This particular embodiment does not employ hem-forming means 56 of the type indicated by the numeral 56 in FIG. 2.

As mentioned previously, the waist and leg openings are elastically contractible or expansible about the torso of a wearer. The leg openings 18 may be dimensioned to be larger than the average baby size and supplemental elastic members 62 may be employed to contract the effective arcuate length of the leg openings to fit the legs of a wearer. Likewise, the waist opening may be sized larger than the waist of a wearer and supplemental elastic gathers attached in a tensioned state to the waist areas 13, 14 to properly size the garment to fit a wearer. An alternative to supplemental elastic gathers at either of the waist and leg openings would be to dimension the stretchable outer cover to fit smaller than the legs and/or waist of a wearer and rely upon the inherent elastomeric stretch properties of the outer cover material to expand to fit the torso of a wearer —this eliminates the need for supplemental gathering of the garment. Where used, such supplemental elastic gathers 62 may comprise strips made of the same material as that of the outer cover, that is, an elastomeric nonwoven laminate of the type described below.

In summary, the outer cover 12 independently functions to make the garment 10 anatomically form-fitting and generally self-adjusting to the wearer while keeping the absorbent insert means 32 positioned in registration against the body so that the insert 32 can, in turn, function to absorb and retain body wastes. It is therefore necessary to attach the insert means 32 to the outer cover so as not to restrict the functional stretchability thereof at least from one of the rear ear portions 20 to the other ear portion 22, in order to achieve desired fit characteristics and present an aesthetic appearance when cross-body outer cover stretchability is relied upon to position the insert means against the body of a wearer. For this purpose, the rear panel, along with the rear waist area, is resiliently stretchable in the cross-body direction 52. The rear ear portions 20, 22 are elongated and with their overlap with the front ear portions 24, 26, there is a full-length closure from the waist opening to each of the leg openings 18. It is this spacing between the leg and waist openings that determines the amount of utilization of cross-body stretchability of the rear panel 30.

Each of the longitudinal ends 42 of the insert further defines an attachment flap, illustrated in FIGS. 19A–19C, which may comprise a coextension of the facing 34 and backing 36 means or the I-shaped reinforcing means 57 (FIG. 4) may be associated with the backing 36 as discussed above. Since the perimeter bond 40 is used to coterminously seal the facing 34 and backing 36 means together and seal the insert against leakage therefrom, the materials used to form the liner and barrier of the facing 34 and backing 36 means, respectively, should be of a polymer which is compatible for autogenous bonding, for example, polypropylene or polypropylene-compatible polymer blends. The member 57 may be any of a number of polyolefin containing foams or other flexible structural supports to facilitate the attachment means, as would be understood by the foregoing discussion.

The garment 10 is preferably fastened about a wearer by a mechanical fastening system employing full-length mechanical closures which maintain the dimensional stability of the spacing between the waist and leg openings, respectively, when the garment is secured about a wearer. Full-length fastening systems of the type disclosed in the above-referenced U.S. Ser. No. 947,941 have been found to be suitable. The preferred fastening system as disclosed in the assignee's above-referenced application requires certain combinations of peel and shear strengths to be useful in conjunction with the garment of the present invention. The garment shown in FIGS. 1, 2, 5, 6 and 8 of the drawings may be a fastening system comprising front 63 and rear 64 pairs of cooperating fastener members. The fastener members shown may be a combination of snap elements separated by tape strips of hook and pile material, such as Velcro TM, or the cooperating fastener members 63 and 64 may comprise other materials having the requisite peel and sheer strengths, for example, a completely hook and pile fastening system. As can be seen from FIGS. 9–12, the rear pair of ears 20, 22 are elongated and tapered slightly, making it easier to reach down under the torso in order to find the ears and bring them over the front panel for fastening.

FIGS. 5–8 show the disposition of the garment of the present invention on a wearer. Generally, the garment presents a neat, trim fit and appearance which is anatomically form-fitting. Because the absorbent insert means is held by the elastomeric outer cover 12 against the body, the garment 10 is also generally self-adjusting to different positions of the wearer, thereby maintaining the form-fitting appearance.

Referring now to FIGS. 12–16, there is depicted a method of using the garment of the present invention wherein a disposable and replaceable fluid-absorbing component is used with a reuseable holder component in an anatomically form-fitting, generally self-adjusting absorbent garment. The method comprises the steps of the providing a resiliently stretchable elastomeric nonwoven outer cover 12 adaptable for holding and positioning the absorbent component, such as the insert means 32, including front 13 and rear 14 waist areas engageable together to define an elastically contractible or expansible waist opening, an intermediate crotch area 16, a pair of elastically contractible leg openings 18 extending along opposed marginal edges of the crotch area 16 and front 28 and rear 30 panels separated from one another by the crotch area 16 (FIG. 12).

Referring to FIG. 13, according to the instant method, an absorbent means 32 is provided which is capable of absorbing and containing bodily fluids and other wastes, defining a shape having opposed longitudinal ends 42 and a pair of sides 44 extending between and interconnecting the ends 42, including a liquid-permeable facing 34, a liquid-impermeable backing 36 coterminous with the facing 34 and an absorbent core 38 disposed therebetween.

Referring further to FIGS. 13–15, the instant method provides cooperable retaining elements on the insert 32 and outer cover 12, respectively, for retention of the insert 32 by the outer cover 12, further including the steps of providing elongated fenestrations 50 in the ends 42 of the insert 32 and providing mating pairs of fastener closures 48 which are fastenable and refastenable with one another on the outer cover 12 and registrable with the fenestrations 50.

With continuing reference to FIG. 13, the insert means 32 is substantially superposed on an inner body-facing surface of the outer cover 12, while aligning the mating fasteners 48 with the fenestrations 50.

Referring to FIG. 15, the garment is integrated together via the retaining means 46, specifically the sliding hem arrangement 56, by engaging the mating pairs of fasteners 48 with one another through aligned ones of the fenestrations 50.

Figure 16:
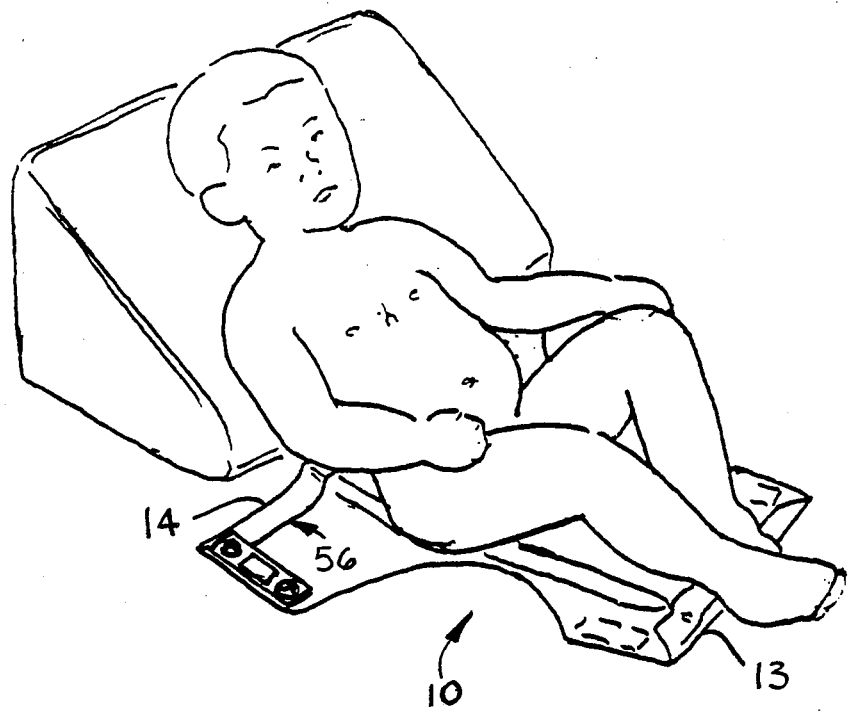
FIG. 16 is a sequential view of FIG. 14 showing a step in the method of using the present invention.

Referring to FIG. 16, the integrated garment is positioned under the lower torso of a wearer with the liquid-permeable facing of the insert means 32 contacting the wearer's skin.

Figure 17:
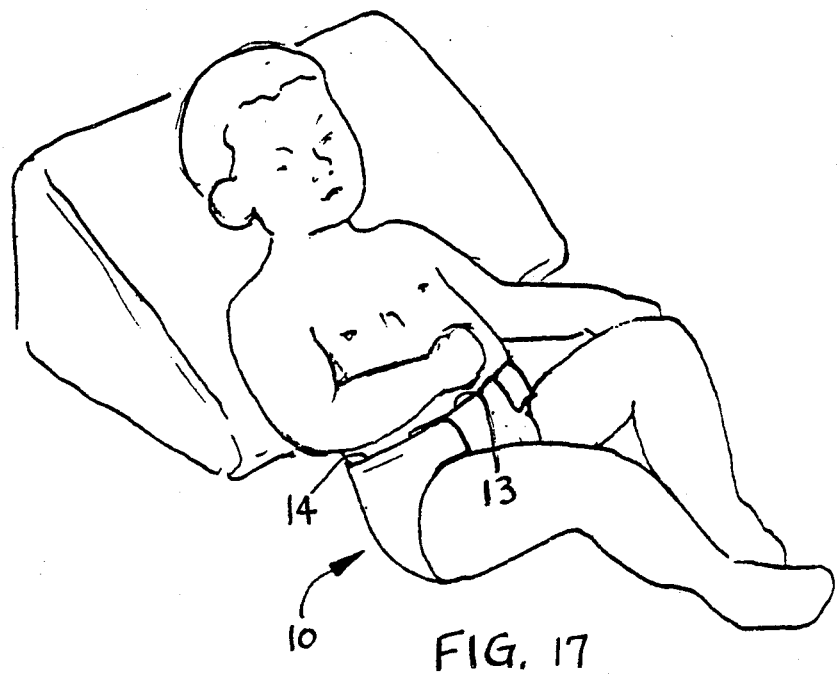
FIG. 17 is a sequential view of FIG. 16 showing a further step in the method of using the present invention.
Figure 18:
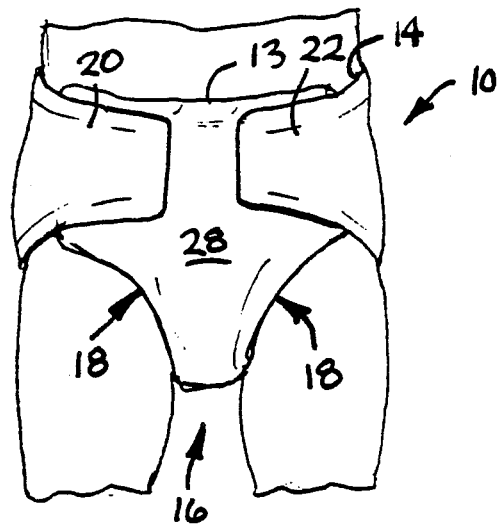
FIG. 18 is a front view of the disposable absorbent garment of the present invention shown secured around a baby according to the method of using the present invention.

Referring to FIG. 17, the method further comprises the step of securing the outermost lateral portions of the waist areas 13, 14 together about the wearer by means of the cooperating pairs of front 64 and rear 63 full-length fasteners which are detailed in FIG. 3.

Because the elastomeric outer cover 12 is allowed to elongate and contract independently of its attachment to the absorbent insert means 32, which is relatively inelastic, the functional positioning characteristics of the outer cover are thereby substantially unrestricted so that the garment stays anatomically form-fitting and generally self-adjusting during the various movements of the wearer.

Since the insert means 32 is comprised of disposable materials, the method of integrating and using the garment may be reversed by disengaging the fasteners 63, 64 and unsecuring the garment 10 from the body, whereupon the mating fasteners 48 may be disengaged from within the fenestrations 50 and the soiled insert 32 removed from the outer cover 12. A fresh insert 32 may then be replaced by following the integration method steps outlined above for another use cycle of the garment.

The integration means shown in FIG. 3A may be employed in an alternative method following essentially the same steps as those outlined in conjunction with FIGS. 13–17 for integrating and using the present garment. A separate integration member generally indicated at 58 bears fastener members 48 on an outwardly facing surface 59 thereof which is selected to correspond to the associated end 42 of the insert in which the fenestrations 50 are formed. The fasteners 48 are then aligned with the fenestrations 50 and engage mating fasteners 48 presented on an inner body-facing surface of a corresponding one of the waist areas.

Another alternative method of using the garment of the present invention also employs a separate integration member shown in FIG. 19C, wherein fenestrations 50 are provided in the waist area 14 of the outer cover and cooperating fastening means 48 are provided on the ends 42 of the insert 32 and on the separate integration member 58. The fastening means on the integration members and ends of the insert are then snapped together through the fenestrations, respectively, to integrate the garment. Referring to FIGS. 19A and 19B, hem-forming means 56 may be provided on the ends 42 of the insert 32 containing cooperating fastening means 48, for example, snaps which are engageable through fenestrations 50 provided in the waist areas of the outer cover, allowing unrestricted functional stretchability of the outer cover relative to the insert.

Turning now to the outer cover 12 of the present invention, which is preferably made from a resiliently stretchable elastomeric nonwoven laminar material having a stretchability of from about 20 percent to about 200 percent. The term stretchability as used herein is defined by the following relationship:

$$\text{stretchability} = ((\text{final dimension} - \text{initial dimension})/\text{initial dimension}) \times 100\%$$

Since the outer cover 12 is also resilient, the outer cover returns essentially to its initial dimension when the stretching force is removed.

One such resiliently stretchable material is disclosed in U.S. Pat. No. 4,663,220 in the name of Tony J. Wisneski and Michael T. Morman, assigned to the assignee of the present application, entitled "Polyolefin-containing Extrudable Compositions and Methods for their Formation Into Elastomeric Products", the disclosure of which is incorporated herein by reference and relied upon. That patent provides extrudable elastomeric compositions which, after extrusion, solidify to form elastomeric products such as, for example, fibrous nonwoven elastomeric webs. The extrudable elastomeric compositions are blends of (1) from at least about 10 percent, by weight, of an A-B-A' block copolymer, where "A" and "A'" are each a thermoplastic polymer endblock which includes a styrenic moiety such as a poly(vinyl arene) and where "B" is an elastomeric poly(ethylene-butylene) midblock, with (2) from greater than 0 percent, by weight, to about 90 percent, by weight, of a polyolefin which, when blended with the A-B-A' block copolymer and subjected to appropriate elevated pressure and elevated temperature conditions, is extrudable, in blended form, with the A-B-A' block copolymer. The A-B-A' block copolymer serves to impart elastomeric properties to products formed from the extrudable composition and the presence of the polyolefin in the blend serves to reduce the viscosity of the composition as compared to the viscosity of the neat, that is, pure, A-B-A' block copolymer and thus enhances the extrudability of the composition.

Preferably, the "A" and "A'" thermoplastic styrenic moiety containing endblocks of the block copolymer are selected from the group including polystyrene and polystyrene homologs such as, for example, poly(alpha-methylstyrene). In some embodiments the "A" and "A'" thermoplastic styrenic moiety containing endblocks are identical. Preferably, the polyolefin is selected from the group including at least one polymer selected from the group including polyethylene, polypropylene, polybutene, ethylene copolymers, propylene copolymers, butene copolymers or blends of two or more of these materials.

The blend usually includes from at least about 20 percent, by weight, to about 95 percent, by weight, of the block copolymer and from at least about 5 percent, by weight, to about 80 percent, by weight, of the polyolefin. For example, the blend may include from about 30 percent, by weight, to about 90 percent, by weight, of the block copolymer and from about 10 percent, by weight, to about 70 percent, by weight, of the polyolefin. Preferably, the blend includes from about 50 percent, by weight, to about 90 percent, by weight, of the block copolymer and from about 10 percent, by weight, to about 50 percent, by weight, of the polyolefin. For example, the blend may include from about 50 percent, by weight, to about 70 percent, by weight, of the block copolymer and from about 30 percent, by weight, to about 50 percent, by weight, of the polyolefin. One blend includes about 60 percent, by weight, of the polyolefin.

The extrudable composition is extruded or otherwise formed, such as, for example, by molding, for example, injection molding, at an appropriate, that is effective, combination of elevated pressure and elevated temperature conditions. These conditions will vary depending on the polyolefin utilized. For example, the extrudable composition should be extruded or otherwise formed at a temperature of at least about 125 degrees Centigrade if polyethylene is utilized as the polyolefin in the blend or at least about 175 degrees Centigrade if polypropylene is utilized in the blend, for example, at a temperature of from at least about 290 degrees Centigrade to about 345 degrees Centigrade, more specifically, at a temperature of from at least about 300 degrees Centigrade to about 335 degrees Centigrade, into elastomeric products such as, for example, elastomeric fibers, which may be collected as a fibrous nonwoven elastomeric web.

Preferably the blends are extrudable within the above-defined temperature ranges at elevated pressures within the die tip, (for example, within the extrusion capillaries of a die tip having thirty (30) extrusion capillaries per lineal inch of die tip with each of the capillaries having a diameter of 0.0145 inches and a length of 0.113 inches) of no more than about 300 pounds per square inch, gage, for example, from pressures of from about 20 pounds per square inch, gage, to about 250 pounds per square inch, gage. More specifically, the blends are extrudable within the above-defined temperature ranges at pressures of from about 50 pounds per square inch, gage, to about 250 pounds per square inch, gage, for example, from about 125 pounds per square inch, gage, to about 225 pounds per square inch, gage. Higher elevated pressures can be utilized with other die designs having a lower number of capillaries per inch of die, but, generally speaking, lower production rates result.

Importantly, it has been found that the extrudable compositions are extrudable at satisfactory throughput rates because the presence of the polyolefin in the extrudable composition reduces the viscosity of the extrudable composition, as compared to the viscosity of the neat, that is, pure, block copolymer, to satisfactory levels. This reduced viscosity proportionally reduces the die tip pressure if all other parameters remain the same. For example, the viscosity of the extrudable compositions will generally be less than about 500 poise when extruded at the above-defined elevated temperature and elevated pressure ranges. Preferably, the viscosity of the extrudable composition is less than about 300 poise when extruded at the above-defined elevated temperatures and elevated pressure ranges. For example, the viscosity of the extrudable composition may be from at least about 100 poise to about 200 poise when extruded at the above-identified elevated temperature and elevated pressure conditions.

Because the polyolefin reduces the viscosity of the blend, as compared to the viscosity of the block copolymer, the extrudable composition is extrudable within the above-identified elevated temperature and elevated pressure ranges, through a die tip having, for example, thirty capillaries per inch of die tip with the capillaries having a diameter of about 0.0145 inches and a length of about 0.113 inches at a rate of from at least about 0.02 grams per capillary per minute to about 1.7 or more grams per capillary per minute. For example, the extrudable composition may be extruded through the above-identified die tip having capillaries with a diameter of about 0.0145 inches and a length of about 0.113 inches at the rate of from at least about 0.1 grams per capillary per minute to about 1.25 grams per capillary per minute. Preferably, the extrudable composition is extrudable through the above-identified die tip having capillaries with a diameter of about 0.0145 inches and a length of about 0.113 inches at the rate of from at least about 0.3 grams per capillary per minute to about 1.1 grams per capillary per minute.

The extrudable composition may be formed into fibrous nonwoven elastomeric webs preferably having microfibers with an average diameter of not greater than about 100 microns, and preferably having an average basis weight of not more than about 300 grams per square meter, for example, an average basis weight of from about 5 grams per square meter to about 100 grams or more per square meter. More specifically, an average basis weight of from about 10 grams per square meter to about 75 grams per square meter. For example, a fibrous nonwoven elastomeric web may be formed by extruding the extrudable composition at an appropriate, that is, effective, combination of elevated temperature and elevated pressure conditions. Preferably, the extrudable composition is extruded at a temperature of from at least about 125 degrees Centigrade if the polyolefin is polyethylene or at least about 175 degrees Centigrade if the polyolefin is polypropylene, for example, from about 290 degrees Centigrade to about 345 degrees Centigrade, more specifically from about 300 degrees Centigrade to about 335 degrees Centigrade. Preferably, the extrudable composition is extruded within the above-identified temperature ranges and pressures, within the die tip, (for example, within the extrusion capillaries of a die tip having thirty (30) extrusion capillaries per lineal inch of die tip with each of the capillaries having a diameter of about 0.0145 inches and a length of 0.113 inches) of no more than about 300 pounds per square inch, gage, for example, from about 20 pounds per square inch, gage, to about 250 pounds per square inch, gage. More specifically, the extrudable composition is extruded at a pressure within the capillaries of the above-identified die tip of from about 50 pounds per square inch, gage, to about 250 pounds per square inch, gage, for example, from about 125 pounds per square inch, gage, to about 225 pounds per square inch, gage.

In the formation of elastomeric nonwoven webs, the extrudable composition is extruded, at the above-defined elevated temperature and elevated pressure conditions at a rate of from at least about 0.02 gram per capillary per minute to about 1.7 or more grams per capillary per minute, for example, from at least about 0.1 gram per capillary per minute to about 1.25 grams per capillary per minute, more specifically, from at least about 0.3 gram per capillary per minute to about 1.1 grams per capillary per minute, through a die having a plurality of small diameter extrusion capillaries, as molten threads into a gas stream which attenuates the molten threads to provide a gas-borne stream of microfibers which are then formed into the fibrous nonwoven elastomeric web upon their deposition on a collecting arrangement. The attenuating gas stream is applied to the molten threads at a temperature of from at least about 100 degrees Centigrade to about 400 degrees Centigrade, for example, from about 200 degrees Centigrade to about 350 degrees Centigrade and at a pressure of from at least about 0.5 pound per square inch, gage, to about 20 pounds per square inch, gage, for example, from at least about 1 pound per square inch., gage, to about 10 pounds per square inch, gage. The thread attenuating gas stream may be an inert, non-oxidizing, gas stream such as, for example, a stream of nitrogen gas. In some embodiments the velocity and temperature of the thread-attenuating gas stream is adjusted so that the fibers are collected as substantially continuous fibers having diameters of from about ten (10) microns to about sixty (60) microns, for example, from at least about ten (10) microns to about forty (40) microns. The fibrous nonwoven elastomeric webs so formed will include elastomeric fibers composed of from at least about 10 percent, by weight, of the block copolymer and greater than 0 percent, by weight, and up to about 90 percent, by weight, of the polyolefin. The fibers are usually composed from at least about 20 percent, by weight, to about 95 percent, by weight, of the block copolymer and from at least about 5 percent, by weight, to about 80 percent, by weight of the polyolefin. For example, the fibers may be composed from at least about 30 percent, by weight, to about 90 percent, by weight, of the block copolymer and from at least about 10 percent, by weight, to about 70 percent, by weight, of the polyolefin. Preferably, the fibers are composed from about 50 percent, by weight, to about 90 percent, by weight, of the block copolymer and from at least about 10 percent, by weight, to about 50 percent, by weight, of the polyolefin. For example, the fibers may be composed from at least about 50 percent, by weight, to about 70 percent, by weight, of the block copolymer and from at least about 30 percent, by weight, to about 50 percent, by weight, of the polyolefin.

Another such resiliently stretchable material is disclosed in U.S. patent application, Ser. No. 760,437 in the name of Jack D. Taylor and Michael J. Vander Wielen and assigned to the assignee of the present application, entitled "Composite Elastomeric Material and Process for Making the Same", the disclosure of which is incorporated herein by reference and relied upon. That application provides a method of producing a composite elastic material comprising at least one gatherable web bonded to at least one elastic web, the method comprising (a) tensioning an elastic web (which may comprise a fibrous web such as a nonwoven web of elastomeric fibers, for example, meltblown elastomeric fibers) to elongate it; (b) bonding the elongated elastic web to at least one gatherable web under conditions which soften at least portions of the elastic web to form a bonded composite web; and (c) relaxing the composite web immediately after the bonding step whereby the gatherable web is gathered to form the composite elastic material. The fibrous elastic web can also be maintained in a stretched condition during the bonding at an elongation of at least about 25 percent, preferably about 25 percent to over 500 percent, for example, about 25 percent to 550 percent elongation during the bonding. The method also includes bonding the elongated elastic web to the gatherable web by overlaying the elastic and gatherable webs and applying heat and pressure to the overlaid webs, for example, by heating bonding sites on the elastic web to a temperature of from at least about 65 degrees Centigrade to about 120 degrees Centigrade, preferably from at least about 70 degrees Centigrade to about 90 degrees Centigrade.

That application also provides an elastic composite material comprising an elastic web bonded to at least one gatherable web which is expansible and contractible with the elastic web upon stretching and relaxing of the composite material, the elastic composite material being made by a method as described above. Also provided is an elastic web that is bonded to the gatherable web at a plurality of spaced-apart locations in a repeating pattern and the gatherable web is gathered between the bonded location. The elastic web may comprise a nonwoven web of elastomeric fibers, preferably elastomeric microfibers, such as, for example, an elastomeric nonwoven web of meltblown elastomeric fibers or an elastomeric film.

The elastic composite material may include one or more of the following in any combination: the elastomeric fibers, preferably meltblown elastomeric fibers, may be formed from material selected from the group including (i) A-B-A' block copolymers wherein "A" and "A'" may be the same or different endblocks and each is a thermoplastic polymer endblock or segment which contains a styrenic moiety such as polystyrene or polystyrene homologs, and "B" is an elastomeric polymer midblock or segment, for example, a midblock selected from the group including poly(ethylene-butylene), polyisoprene and polybutadiene, with poly(ethylene-butylene) being preferred and (ii) blends of one or more polyolefins with the A-B-A' block copolymers of (i) where "B" is a poly(ethylene-butylene) midblock; each of the "A" and "A'" endblocks may be selected from the group consisting of polystyrene and polystyrene homologs, for example, poly(alpha methylstyrene), and where the elastomeric fibers are formed from a blend of one or more polyolefins with an A-B-A' block copolymer where "B" is a poly(ethylene-butylene) midblock, the polyolefin is selected from one or more of polyethylene, polypropylene, polybutene, ethylene copolymers, propylene copolymers and butene copolymers; the elastomeric film and the elastomeric fibers which form the elastomeric nonwoven web, for example, the meltblown microfibers, are composed of at least 10 percent, for example at least 20 percent, more specifically at least 30 percent, for example, from about 10 percent to 90 percent, by weight, of the aforesaid A-B-A' block copolymers and greater than 0 percent, by weight, for example, from about 90 percent to about 10 percent, by weight, of the polyolefin; the elastic web, for example, a fibrous elastic web, is bonded to the gatherable web at a plurality of spaced-apart locations in a repeating pattern and the gatherable web is gathered between the bonded locations; the elastic web preferably has a low basis weight of from about 5 to about 300, preferably from about 5 to about 200, grams per square meter, for example, from about 5 to about 100 grams per square meter, although its basis weight can be much higher; the gatherable web is a nonwoven, non-elastic material, preferably one composed of fibers formed from materials selected from the group including polyester fibers, for example, poly(ethylene terephthalate) fibers, polyolefin fibers, polyamide fibers, for example, nylon fibers, cellulosic fibers, for example, cotton fibers, and mixtures thereof. Alternatively, the gatherable web may be any suitable woven fabric. In a particular aspect, the composition of the A-B-A' polymer used is such that the sum of the molecular weight of "A" with the molecular weight of "A'" is from about 14 to 31 percent (from about 14 to 29 percent when "B" is poly(ethylene-butylene)) of the molecular weight of the A-B-A' block copolymer.

A further such resiliently stretchable material is disclosed in U.S. Pat. No. 4,657,802, in the name of Michael J. Morman, and assigned to the assignee of the present invention, entitled "Composite Nonwoven Elastic Web", the disclosure of which is incorporated herein by reference. That patent is directed to a process for producing a composite nonwoven elastic web which is composed of a nonwoven elastic web that is joined to a fibrous nonwoven gathered web. In particular, the process disclosed therein produces a composite nonwoven elastic web which, in its relaxed, nonstretched state, is composed of a gathered nonwoven fibrous web that is joined to a nonwoven elastic web with the nonwoven elastic web having been relaxed from a stretched, biased length to a relaxed, unbiased, nonstretched length so as to gather the fibrous nonwoven gathered web. An important feature of the process disclosed therein is that the fibrous nonwoven gatherable web is formed directly onto a surface of the nonwoven elastic web while the nonwoven elastic web is maintained in a stretched, biased and elongated condition. The nonwoven elastic web may be formed by, for example, a meltblowing process or any other process for forming a nonwoven elastic web. For example, the nonwoven elastic web could be an apertured web of an elastic film as opposed to a meltblown fibrous nonwoven elastic web. The formed nonwoven elastic web has a normal relaxed, nonstretched, nonbiased length. Thereafter, the nonwoven elastic web is elongated by being stretched to a stretched, biased length. In a subsequent step of the process a fibrous nonwoven gatherable web may be formed, for example, by either a meltblowing or spunbonding process or any other process for forming a fibrous nonwoven gatherable web, directly upon a surface of the nonwoven elastic web while the nonwoven elastic web is maintained at its elongated, stretched and biased length. During formation of the fibrous nonwoven gatherable web the nonwoven elastic web is maintained at a stretched length which is at least about 125 percent, that is, at least about one and one quarter of the relaxed, unbiased length of the nonwoven elastic web. For example, the stretched, biased length of the nonwoven elastic web may be maintained in the range of from at least about 125 percent of the relaxed, unbiased length of the nonwoven elastic web to about 700 or more percent of the relaxed, unbiased length of the nonwoven elastic web. The fibrous nonwoven gatherable web is joined to the nonwoven elastic web while the nonwoven elastic web is maintained at its elongated stretched, biased length. This results in the formation of a composite nonwoven elastic web which includes the nonwoven elastic web which is joined to the fibrous nonwoven gatherable web. Because the fibrous nonwoven gatherable web is formed directly onto the surface of the nonwoven elastic web while the nonwoven elastic web is being maintained at its stretched, biased length, the nonwoven elastic web is, at this stage in the process, elongated, stretched and biased and the fibrous nonwoven gatherable web is in an ungathered but gatherable condition. In one aspect, the joining of the fibrous nonwoven gatherable web to the nonwoven elastic web is achieved by heat-bonding to fuse the two webs to each other. The heat-bonding may be carried out within the temperature range of from about 50 degrees centigrade below the melt temperature of at least one of the materials utilized to form at least one of the two webs to about the melt temperature of at least one of the materials utilized to form at least one of the two webs. At high through-put rates the heat-bonding can be carried out above the melt temperature of one or more of the materials utilized to form the webs. The heat-bonding may also be carried out under appropriate conventional pressurized conditions. If desired, conventional sonic bonding techniques may be substituted for the heat-bonding steps.

The patent also discloses another embodiment whereby the joining of the fibrous nonwoven gatherable web to the stretched nonwoven elastic web is achieved solely by the entanglement of the individual fibers of the fibrous nonwoven gatherable web with the nonwoven elastic web during formation of the fibrous gatherable web on the surface of the elastic web. If the nonwoven elastic web is a fibrous nonwoven elastic web formed by, for example, meltblowing, entanglement of the individual fibers of the fibrous nonwoven gatherable web with the fibrous nonwoven elastic web is achieved by entanglement of the individual fibers of the fibrous gatherable web with the individual fibers of the fibrous elastic web. If the nonwoven elastic web is an apertured film, joining of the fibrous nonwoven web with the film is achieved by entanglement of the individual fibers of the fibrous gatherable web within the apertures of the film. The joining of the two webs to each other can also be achieved by forming the nonwoven elastic web out of a tacky elastic material, a process that will be discussed hereinafter. In addition, the joining of the two webs to each other may be further enhanced by applying pressure to the two webs after the gatherable web has been formed on the surface of the elastic web. Further improvement in the joining of the two webs can be obtained by applying an adhesive material to the upper surface of the nonwoven elastic web prior to formation of the fibrous nonwoven gatherable web thereon.

After joining of the two webs to each other has been achieved to form a composite elastic web, the biasing force is removed from the composite nonwoven elastic web and the composite elastic web is allowed to relax to its normal relaxed, unbiased length. Because the fibrous nonwoven gatherable web is joined to the nonwoven elastic web while the nonwoven elastic web is stretched, relaxation of the composite nonwoven elastic web results in the gatherable web being carried with the contracting nonwoven elastic web and thus being gathered. After gathering of the fibrous nonwoven gatherable web has occurred by reducing the biasing force on the composite nonwoven elastic web, the composite nonwoven elastic web may be rolled up in rolls for storage and shipment of directed to a manufacturing process for the production of products such as the disposable garments taught by the present application.

As indicated above, the process disclosed in U.S. Pat. No. 4,657,802 can be enhanced by the utilization of a tacky fibrous nonwoven elastic web which can be formed by, for example, meltblowing microfibers of a tacky elastic material such as, for example, an A-B-A' block copolymer or blends of such A-B-A' block copolymers with poly(alpha-methylstyrene) where "A" and "A'" are each thermoplastic polystyrene or polystyrene homolog endblocks and "B" is an elastic polyisoprene midblock. In some embodiments "A" may be the same thermoplastic polystyrene or polystyrene homolog endblock as "A'". The tacky fibrous nonwoven elastic web is then elongated by being stretched to an elongated, stretched length and a fibrous nonwoven gatherable web is formed, for example, by meltblowing or spunbonding the fibrous nonwoven gatherable web, directly upon a surface of the tacky fibrous nonwoven elastic web while maintaining the fibrous nonwoven elastic web at its stretched length. As a result of the fact that the fibrous nonwoven elastic web is tacky, the fibrous nonwoven gatherable web is simultaneously formed upon and adhesively joined to the surface of the tacky fibrous nonwoven elastic web. This results in the formation of a composite nonwoven elastic web having an ungathered fibrous gatherable web adhesively joined to the tacky fibrous nonwoven elastic web with the joining of the two webs to each other being achieved by the adhesive joining which occurs during formation of the fibrous nonwoven gatherable web on the surface of the fibrous nonwoven elastic web. The adhesive joining of the two webs to each other may be increased upon application of pressure to the composite nonwoven elastic web by passing the composite nonwoven elastic web through the nip between rollers, which may be unheated, after the composite web has been formed but before the fibrous tacky nonwoven elastic web is allowed to relax. The adhesive joining may be further enhanced by application of an adhesive material to the surface of the tacky fibrous nonwoven elastic web prior to formation of the gatherable web thereon. The composite nonwoven elastic web is then allowed to relax to its normal relaxed, unbiased length. Because the fibrous nonwoven gatherable web is joined to the tacky fibrous nonwoven elastic web while the tacky fibrous nonwoven elastic web is in a stretched condition, relaxation of the composite nonwoven elastic web and thus the tacky fibrous nonwoven elastic web results in the gatherable web being carried with the contracting fibrous nonwoven elastic web and thus being gathered. After gathering of the fibrous nonwoven gatherable web has occurred the composite nonwoven elastic web may be rolled up in rolls for storage or directly applied to a manufacturing process for the production of disposable garments such as the disposable garments taught by the present application.

The U.S. Pat. No. 4,657,802 is also directed to a composite nonwoven elastic web composed of a nonwoven elastic web that is joined to a gatherable fibrous nonwoven web which has been gathered and with the composite web having been formed by any of the embodiments of the process disclosed above. In particular, the composite nonwoven elastic web, in its relaxed, nonstretched state, is composed of a nonwoven elastic web that is joined to a fibrous nonwoven gathered web which has been gathered as a result of the nonwoven elastic web having been relaxed from an elongated stretched, biased length to a relaxed, unbiased nonstretched length. Exemplary elastomeric materials for use in formation of the fibrous nonwoven elastic web include polyester elastomeric materials, polyurethane elastomeric materials, and polyamide elastomeric materials. Other elastomeric materials for use in formation of the fibrous nonwoven elastic web include (a) A-B-A' block copolymers, where "A" and "A'" are each a thermoplastic polymer endblock which includes a styrenic moiety and where "A" may be the same thermoplastic polymer endblock as "A'", such as a poly(vinyl arene), and where "B" is an elastomeric polymer midblock such as a conjugated diene or a lower alkene or (b) blends of one or more polyolefins or poly(alpha-methyl styrene) with A-B-A' block copolymers, where "A" and "A'" are each a thermoplastic polymer endblock which includes a styrenic moiety, where "A" may be the same thermoplastic polymer endblock as "A'", such as a poly(vinyl arene) and where "B" is an elastomeric polymer midblock such as a conjugated diene or a lower alkene. The "A" and "A'" endblocks may be selected from the group including polystyrene and polystyrene homologs and the "B" midblock may be selected from the group including polyisoprene, polybutadiene or poly(ethylene-butylene). If "A" and "A'" are selected from the group including polystyrene or polystyrene homologs and "B" is poly(ethylene-butylene), materials which may be blended with these block copolymers are polymers, including copolymers of ethylene, propylene, butene, other lower alkenes or one or more of these materials. If "A" and "A'" are selected from the group including polystyrene or polystyrene homologs and "B" is a polyisoprene midblock, a material for blending with this type of block copolymer is poly(alpha-methylstyrene).

As used in the U.S. patent application Ser. No. 760,449, and as contemplated herein, the term "nonwoven web" or "nonwoven layer" includes any web of material which has been formed without use of textile weaving processes which produce a structure of individual fibers which are interwoven in an identifiable repeating manner. Specific examples of nonwoven webs would include, without limitation, a meltblown nonwoven web, a spunbonded nonwoven web, an apertured film, a microporous web, elastomeric netting or a carded web of staple fibers.

It is to be clearly understood that the descriptions of methods for making a material suitable for outer cover 12 and the description of materials suitable for the outer cover 12 are exemplary only and not meant to be limiting. As discussed previously, the material of the laminar leg elastics 62 may also be used as the outer cover material and, conversely, the outer cover material may be used as the leg elastic material.

The bodyside liner 34 may be airlaid, a bonded carded web, a powder-bonded carded web or a pattern bonded, spunbonded web of synthetic fibers such as polypropylene, polyester and the like.

Various materials are contemplated for use as the absorbent core 38, including fibrous materials, foams, particulates, etc. In general, the most economical liquid absorbent material for use in disposable diapers has been an absorbent fiber. The absorbent fiber most commonly used is cellulosic fiber such as comminuted wood pulp, commonly known in the art as "pulp fluff," or simply "fluff."

Comminuted wood pulp (fluff) is preferred as an absorbent fiber, but other cellulose fibers such as cotton linters can be used. The preferred fluff is southern pine kraft wood pulp (i.e., made according to the sulfate process commonly known in the art) which has been bleached, such as can be purchased from International Paper Company. Other softwood fluffs may be purchased from Kimberly-Clark Corporation, such as CR-54. Various hardwood fluffs may also be blended with the softwood fluffs to form the absorbent composite. A water-swellable hydrogel material, preferably in particulate form, may be used in a number of various arrangements within the absorbent core 38 in order to decrease the bulkiness and enhance the capacity thereof. It should be understood that additional elements could be provided in conjunction with those already set forth, without departing from the contemplated scope of the present invention and the description herein is not intended to be in any way limiting.

We claim:

1. A method of integrating a fluid-absorbing component into a holding component of an anatomically form-fitting and generally self-adjusting diaper garment, said method comprising the steps of:
   a. providing a flexible, resiliently stretchable positioning means for holding and positioning the absorbing component during use, delimiting a shape having front and rear waist sections, an intermediate crotch section, a pair of leg openings along opposed marginal edges of said crotch section and front and rear panels separated from one another by said crotch section;
   b. providing a relatively inelastic insert means containing said fluid-absorbing component for absorbing and containing bodily fluids and other wastes, delimiting a shape, superposable on an inner, body-facing surface of said positioning means, with opposed longitudinal ends and a pair of sides extending between and interconnecting said ends;
   c. providing cooperable retaining means on said insert means and said positioning means, respectively, for retaining said insert means, including fastening means and slot-forming means adapted for receiving said fastening means therethrough while allowing substantially unrestricted functional elongation and retraction of said positioning means relative to said insert means;
   d. providing a flexible shape-retaining means disposed with said inelastic insert means for maintaining said inelastic insert means in a generally body-conforming orientation;
   e. superposing said insert means on said inner surface of said positioning means; and
   f. fastening said fastening means together through said slot-forming means, integrating said insert means with said outer cover means and forming said diaper garment.

2. The method of claim 1 further comprising the step of providing said fastening means with fastenable and refastenable closure means and providing a disposable insert means adapted for removal and replacement thereof.

3. The method of claim 1 or 2 wherein said slot-forming means define one or more elongated fenestrations for receiving said fastening means.

4. The method of claim 1 wherein said positioning means comprise an outer cover which is resiliently stretchable either in a direction essentially parallel to a line centered on the longitudinal axis of said garment, a cross-body direction essentially transverse to the longitudinal axis of said garment or in both of said directions.

5. The method of claim 4 wherein said outer cover means is resiliently stretchable in said cross-body direction.

6. The method of claim 4 wherein said outer cover means is resiliently stretchable in said longitudinal direction.

7. The method of claim 5 wherein said waist sections are resiliently stretchable in said cross-body direction.

8. The method of claim 7 wherein either of said front and rear panels are resiliently stretchable in said cross-body direction.

9. The method of claim 7 wherein either of said front and rear panels and said crotch section are resiliently stretchable in said longitudinal direction.

10. The method of claim 7 or 9 wherein said slot-forming means define one or more elongated fenestrations adapted for receiving said fastening means therethrough for substantially unrestricted elongation and retraction of said outer cover relative to said insert means in a direction parallel to the major axis of said one or more elongated fenestrations.

11. The method of claim 10 further comprising a plurality of said fenestrations for receiving a corresponding plurality of said fastening means therethrough.

12. The method of claim 10 further comprising the step of providing said slot-forming means in said insert means.

13. The method of claim 10 wherein said fastening means comprise cooperating closure means, releasably engageable with one another through said fenestrations, for allowing removal and replacement of said insert means.

14. The method of claim 13 wherein said insert means further comprises liquid-impermeable barrier means, liquid-permeable liner means coterminous with said barrier means and a fluid-absorbing core means disposed therebetween.

15. The method of claim 10 wherein said outer cover comprises an elastomeric nonwoven fabric.

16. The method of claim 10 wherein said outer cover is breathable.

17. The method of claim 16 wherein said outer cover comprises an elastomeric nonwoven fabric.

18. The method of claim 10 wherein said elastomeric outer cover comprises a laminar fabric wherein an elastic layer is joined to one or more gatherable layers.

19. The method of claim 18 wherein either of said elastic and gatherable layers comprise a nonwoven web.

20. The method of claim 19 wherein said nonwoven web comprises polymeric fibers consisting essentially of one or more materials selected from a group containing: polyolefins and A-B-A' block copolymers.

21. The method of claim 10 wherein said fastening means are on said outer cover.

22. The method of claim 21 further comprising a separate retention member presenting fastening means cooperable with said fastening means on said outer cover.

23. The method of claim 22 wherein said cooperating said fastening means on said separate retention member and said outer cover comprise releasable closure means fastenable and refastenable with one another, allowing removal and replacement of said insert means.

24. A method of integrating a disposable fluid-absorbing component into a reusable holding component of an anatomically form-fitting, generally self-adjusting diaper garment, said method comprising the steps of:
  a. providing a flexible, elastomeric nonwoven fabric outer cover for holding and positioning the absorbing component during use, including front and rear waist sections each resiliently stretchable in a cross-body direction essentially transverse to a line centered on the longitudinal axis of said garment, an intermediate crotch section, a pair of leg openings elastically contractible or expansible along opposed marginal side edges of the crotch section and front and rear panels separated by the crotch section;
  b. providing a relatively inelastic absorbent insert structure adapted for containing the absorbing component for absorbing and containing bodily fluids and other wastes, the insert delimiting a shape superposable on the outer cover and having opposed longitudinal ends with a pair of sides extending between and interconnecting the ends;
  c. providing a slidable retaining mechanism for retention of the insert within the outer cover, including fastening closures fastenable and refastenable with one another and one or more corresponding fenestrations adapted for receiving the cooperating closures therethrough, allowing removal and replacement of the insert while allowing substantially unrestricted elongation and retraction of the outer cover relative to the insert;
  d. providing a flexible shape-retaining means disposed with said inelastic absorbent insert structure for maintaining said inelastic absorbent insert structure in a generally body-conforming orientation;
  e. superposing the insert on an inner, body-facing surface of the outer cover; and
  f. registering and engaging the fastener closures together through the one or more fenestrations, integrating the insert with the outer cover to form the absorbent garment.

25. The method of claim 24 further comprising the step of providing a slidable retaining mechanism for retention of the insert within the outer cover, including providing elongated fenestrations in the waist sections and a hem containing cooperable fastening closures on an externally-facing surface of the ends of the insert, folding the hem outwardly and entrapping the waist sections while aligning the fastening closures with corresponding ones of the fenestrations, then fastening the closures together therethrough.

26. The method of claim 24 further comprising the steps of providing a hemmed waist opening along the waist sections, disposing the cooperating fastener closures opposite one another inside the hem, forming the fenestrations along the ends of the insert, folding the hem over the ends so that the closures are in registration with the fenestrations and then engaging the closures together through the fenestrations.

27. The method of claim 24 further comprising the step of providing a separate integration member having fastener closures thereon and providing mating fastener closures along the waist sections, the mating pairs of fastener closures being registrable with the one or more fenestrations, aligning each of the mating pairs of closures with one another and with an associated fenestration, then engaging the closures together through the fenestrations.

28. The method of claim 24 further comprising the step of providing one or more fenestrations elongated in the cross-body direction in the waist sections, providing fastener closures at the ends of the insert on an externally-facing surface thereof, providing a separate integration member having mating closures thereon, the mating pairs of closures being registrable with the one or more fenestrations, aligning each of the mating pairs of closures with one another and with associated ones of the fenestrations, then engaging the closures together through the fenestrations.

* * * * *